(12) United States Patent
Jaramillo et al.

(10) Patent No.: US 8,882,715 B2
(45) Date of Patent: Nov. 11, 2014

(54) CATHETERIZATION DEVICE AND METHOD

(76) Inventors: Carlos Jaramillo, Tampa, FL (US);
Timothy M. Holt, New Port Richey, FL (US)

( * ) Notice: Subject to any disclaimer, the term of this patent is extended or adjusted under 35 U.S.C. 154(b) by 1745 days.

(21) Appl. No.: 11/823,569

(22) Filed: Jun. 28, 2007

(65) Prior Publication Data

US 2008/0027390 A1    Jan. 31, 2008

Related U.S. Application Data

(60) Provisional application No. 60/834,474, filed on Jul. 31, 2006.

(51) Int. Cl.
*A61M 5/178*    (2006.01)
*A61B 17/34*    (2006.01)

(52) U.S. Cl.
CPC .................. *A61B 17/3415* (2013.01)
USPC .................................... 604/170.03

(58) Field of Classification Search
CPC .................................................. A61B 17/3415
USPC ............... 604/22, 21, 164.01, 164.08, 164.12, 604/170.02, 170.03, 164.06, 164.13
See application file for complete search history.

(56) References Cited

U.S. PATENT DOCUMENTS

| | | | |
|---|---|---|---|
| 2,118,631 A | 5/1938 | Wappler | |
| 3,608,539 A * | 9/1971 | Miller | 600/567 |
| 3,719,737 A | 3/1973 | Vaillancourt et al. | |
| 4,468,224 A | 8/1984 | Enzmann et al. | |
| 4,509,945 A * | 4/1985 | Kramann et al. | 604/164.13 |
| 4,808,156 A | 2/1989 | Dean | |
| 4,882,777 A * | 11/1989 | Narula | 604/532 |
| 4,909,793 A * | 3/1990 | Vining et al. | 604/164.08 |
| 5,044,369 A | 9/1991 | Sahota | |
| 5,209,742 A | 5/1993 | Venema et al. | |
| 5,562,633 A * | 10/1996 | Wozencroft | 604/171 |
| 5,663,051 A * | 9/1997 | Vlasselaer | 435/7.23 |
| 5,902,289 A | 5/1999 | Swartz et al. | |
| 6,379,346 B1 | 4/2002 | McIvor et al. | |
| 6,626,868 B1 * | 9/2003 | Prestidge et al. | 604/158 |
| 2001/0021824 A1 * | 9/2001 | Marsh et al. | 604/164.09 |
| 2004/0111063 A1 * | 6/2004 | Botich et al. | 604/195 |
| 2005/0283125 A1 | 12/2005 | Barkhahn et al. | |
| 2007/0005019 A1 * | 1/2007 | Okishige | 604/175 |

FOREIGN PATENT DOCUMENTS

| | | |
|---|---|---|
| EP | 0898480 B1 | 9/2003 |
| WO | 9702066 A1 | 1/1997 |
| WO | 0102047 A1 | 1/2001 |

* cited by examiner

*Primary Examiner* — Kami A Bosworth
*Assistant Examiner* — Imani Hayman
(74) *Attorney, Agent, or Firm* — Defillo & Associates, Inc; Evelyn A. Defilló

(57) ABSTRACT

An improved catheterization device of the type in which a flexible catheter overlays a rigid or semi-rigid stylet, the improvement residing in the preformed arcuate curvature of the stylet, the curvature of which can be in the form of a circular arc, an elliptical arc, or an irregular curvature, for facilitating insertion of the catheter into the blood vessel of a subject with reduced risk of vascular damage or where the direct path to the blood vessel is obstructed, and methods for its use.

12 Claims, 4 Drawing Sheets

CATHETERIZATION DEVICE AND METHOD

CROSS-REFERENCE

The present application claims priority from U.S. Provisional Patent Application No. 60/834,473 filed Jul. 31, 2006, the contents of which are hereby incorporated in their entirety by reference, and which is not admitted to be prior art by its mention in the background.

FIELD OF THE INVENTION

The invention relates to a system for placing a catheter in a blood vessel, and more particularly to an improved catheterization device of the catheter-over-needle type and to a method for its use.

BACKGROUND OF THE INVENTION

Placement of a catheter into a blood vessel of a human patient may be performed for a variety of medical, therapeutic and diagnostic purposes. For example, percutaneous insertion of a catheter into the jugular or subclavian vein is often performed to enable measurement of central venous pressure or to facilitate total intravenous feeding or to administer other intravenous therapy.

Percutaneous insertion of a catheter (herein "catheterization") into a blood vessel generally involves the use of a catheter-over-needle or a catheter-through-catheter placement technique. The catheter-over-needle placement technique generally uses a catheter of up to about four inches in length that has a tapered end with a sharp, straight needle or stylet extending from the tapered end. The needle or stylet is inserted into a blood vessel, after which the needle or stylet is withdrawn. The catheter may then be pushed further along the blood vessel.

Difficulties in catheterizing certain kinds of patient may arise using a catheter-over-needle technique. Elderly patients or drug-abusers may have veins that are particularly susceptible to needle damage, either from fragility or prior abuse. Also, in obese patients the correct depth of needle or stylet insertion may be difficult to assess, resulting in an increased probability that the blood vessel may be missed or penetrated completely resulting in vessel damage and bleeding into the surrounding tissues.

Difficulties in catheterization using prior art devices may also arise where direct access to a target blood vessel is blocked by bone or other obstruction as may occur, for example, in catheterization of a subclavian vein.

Catheterization of blood vessels oriented substantially parallel to the skin can be problematic because insertion of the needle or stylet at a large acute angle relative to the skin results in penetration of the blood vessel wall at a corresponding large acute angle and increased probability of damage or penetration of the opposite blood vessel wall. While this problem may be somewhat ameliorated by inserting the needle or stylet into the skin at a small acute angle, this technique either increases the length of the catheterization device required or reduces the length of the catheter that is available for insertion into the blood vessel.

Further, the catheter-over-needle technique requires that the needle or stylet and the overlaying catheter must be handled carefully during catheterization to minimize the risk of damage to the wall of the catheter. Thus, for example, flexing of the stylet should be avoided.

While elaborate devices and techniques are known for the guidance of catheters once inserted into a blood vessel (see, e.g., U.S. Pat. Nos. 4,468,224, and 6,379,346 B1), and for the production of catheters capable of assuming a desired shape once the needle or stylet is withdrawn (see, e.g., U.S. Pat. Nos. 3,719,737 and 5,044,369), these approaches do not address the difficulties described above relating to initial catheterization.

Therefore, notwithstanding the existence of a variety of catheterization devices in the prior art, there is a continuing need for a device that permits catheterization of veins for which a direct approach is blocked by bone or other obstruction, and for a device that lessens the risk of vein wall damage in catheterization of blood vessels of drug abusers, the obese, and the elderly, and the present invention substantially fulfills these needs. All this and more will become apparent to one of ordinary skill, upon reading the disclosure, drawings, and claims appended hereto.

SUMMARY OF THE INVENTION

The present invention is directed to a catheterization device, and method for its use, that satisfies the above need for improved catheterization of veins for which a direct approach is blocked, and for a device that lessens the risk of vein wall damage in catheterization of blood vessels of drug abusers, the obese, and the elderly. The inventors have surprisingly found that a device in which the stylet comprises a preformed arc along substantially its entire length satisfies at least the aforementioned needs.

In a first embodiment, the device comprises a flexible catheter, the proximal end of which is mounted to the distal end of a tubular fitting, such as for example a female luer fitting, with the interior surfaces of the catheter and the fitting in fluid communication. The device further comprises a preformed arcuate stylet comprising a tip adapted for penetrating tissue. The stylet is disposed within the catheter and the tip of the stylet extends from the distal end of the catheter. A sealing member seals the proximal end of the fitting in a readily detachable manner.

In a second embodiment, the device optionally further comprises a detachable covering mounting to the sealing member to substantially enclose and protect the catheter, stylet, and fitting when not in use.

In a third embodiment, the device optionally comprises a means for retracting the stylet into the sealing member. For example, the stylet can be operably connected to a preloaded spring and trigger housed within the sealing member whereby operation of the trigger causes the spring to retract the stylet into the sealing member for safety.

In a fourth embodiment, the arc of the stylet is selected from circular, elliptical, and irregular arcs.

In a fifth embodiment, a method for blood vessel catheterization is provided for using the catheterization device of the present invention. The tip of the stylet is first positioned upon the skin of a subject proximal to a blood vessel. The tip of the stylet and at least a portion of the overlying catheter are inserted into the blood vessel by causing the tip to substantially follow the arcuation of the stylet in its passage from the skin to the blood vessel. The stylet is withdrawn from the catheter to leave the catheter in place. The sealing member is detached. It will be apparent that, according to the particular construction of the device, the steps of the preceding method can be performed in alternative orders, all of which are envisaged as being within the scope of the present invention.

It is therefore an object of the present invention to provide an improved catheterization device, and method for its use, for increased ease of catheterization of blood vessels for which the direct pathway for catheterization is obstructed by bone or other obstruction.

It is a further object of the present invention to provide an improved catheterization device that reduces the likelihood that a vein will be damaged or passed through during catheterization.

BRIEF DESCRIPTION OF THE DRAWINGS

These and other features, aspects, and advantages of the present invention will become better understood with reference to the following description, claims, and accompanying drawings, where:

DETAILED DESCRIPTION

Certain exemplary but non-limiting embodiments of the present invention will now be described with reference to the attached drawings.

Figure 1:
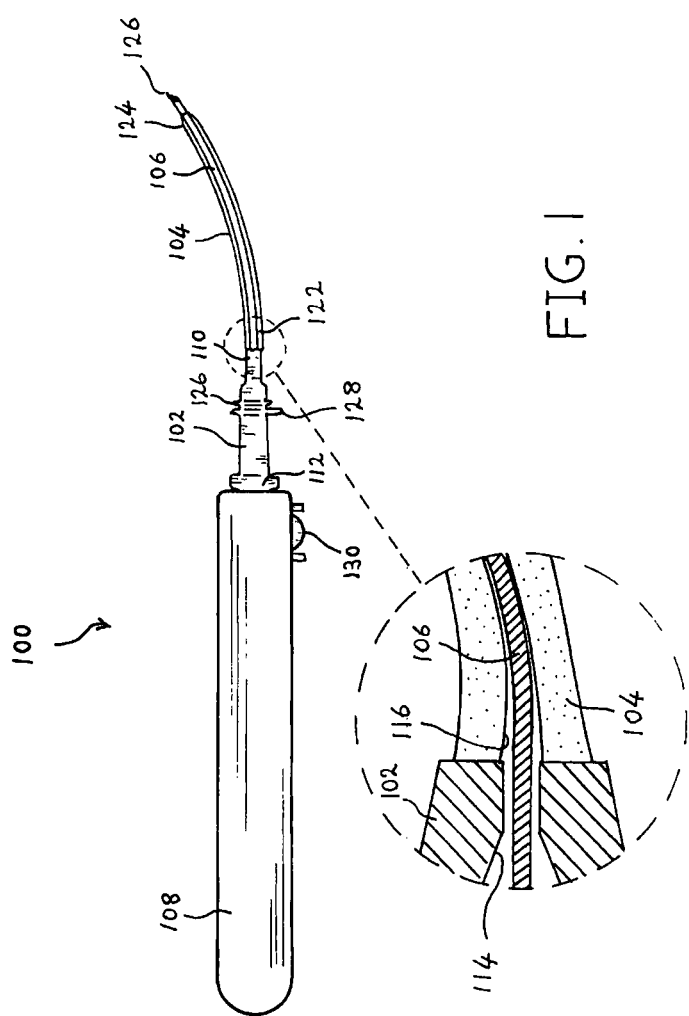
FIG. 1 shows a perspective view of an embodiment of the catheterization device according to the present invention. Inset: a sectional view of circled portion.

Referring now to FIG. 1, there is shown an embodiment of a catheterization device 100 according to the present invention. The device 100 comprises a tubular fitting 102, a flexible catheter 104, a preformed arcuate stylet 106, and a sealing member 108.

Tubular fitting 102 can be formed from any rigid or semi-rigid material, such as a plastic or metal, provided that the material is capable of forming a self-supporting fitting having a proximal end adapted for mounting to a means of fluid delivery or collection, such as a syringe tip or the connector of an intravenous drip. Preferably, tubular fitting 102 is a luer fitting, as is known in the art, and most preferably fitting 102 is a female luer fitting. The distal end 110 of the tubular fitting 102 is optionally narrower than proximal end 112, and has a diameter similar to or greater than the diameter of flexible catheter 104. Between the proximal 112 and distal 110 ends, the fitting 102 comprises an inner surface 114. The tubular fitting 102 optionally comprises other desirable features such as, for example, one or more projections 126 providing improved grip and features 128 for securing the fitting to the means of fluid delivery or fluid collection.

Flexible catheter 104 can be formed of any biocompatible flexible material, such as medical grade silicone rubber, polyurethane, polyethylene polyvinyl chloride, Teflon™, siliconised latex, or the like. The proximal end 122 of the catheter 104 is mounted to the distal end 110 of fitting 102 to permit leak-free, fluid communication between the inner surface of the fitting 114 and the inner surface of the catheter 116. The distal end 124 of the catheter 104 is optionally tapered or otherwise shaped or treated for improved penetration of tissue and for reduced damage to vessel walls.

Arcuate stylet 106 can be preformed from any sufficiently rigid material capable of forming a slender arcuate body for penetration of tissue by tip 126. The stylet 106 can, for example, be formed from a metal such as stainless steel, or from a rigid polymeric material. Preferably, the stylet 106 is a tubular body such as a syringe needle comprising a hollow-ground point. The arcuate stylet 106 is preformed in the shape of an arc of a circle, or an arc of an ellipse, or an irregular arcuate form. The term "preformed" as used herein refers to the manufacture of an arcuate stylet prior to its combination with an overlying catheter. In embodiments comprising an arcuate form that is the arc of a circle, the radius of the arc is preferably between about 1.5 inches to about 12 inches. In other embodiments, the arcuate form of the stylet can be in the form of an elliptical arc according to known mathematical equations for ellipses. The stylet can also comprise an arc that does not conform to any simple mathematical equation, which is herein termed an "irregular" form (FIG. 3E). More specifically, the choice of arcuate form may be a matter of user preference or may be determined by physiological constraints at specific catheterization sites and/or types of patient, such as, for example, subclavian or jugular catheterization of minors, adults, or animals.

Stylet 106 is disposed in the lumen of the catheter 104, preferably for at least the length of the catheter, and the tip 126 of the stylet protrudes from the distal end 124 of the catheter. The catheter 104 thereby conforms to the arcuate shape of the stylet 106 at least until the stylet 106 is withdrawn.

Sealing member 108 mounts to the proximal end 112 of the fitting 102, for example to aid sterility, until the proximal end 112 is exposed in use. The shape and material of the sealing member 108 are not particularly limited, and can be, for example, in the form of a tube closed at one end, or a simple plastic or metal plug. In the exemplary embodiments shown in FIGS. 1 and 2, one end of stylet 114 is retained in the sealing member 108 which helps retain the sealing member 108 over proximal end 112 of the fitting until the stylet 106 and sealing member 108 are removed as an assembly.

Figure 2:
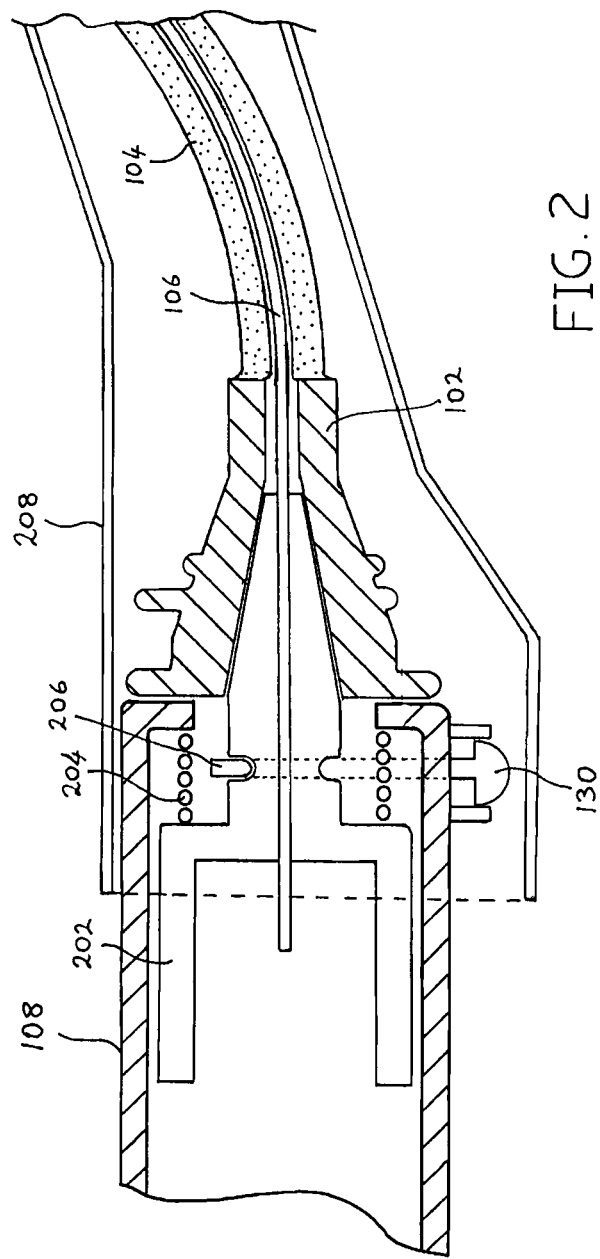
FIG. 2 shows longitudinal cross-sectional view of the catheterization device according to FIG. 1, further comprising an optional detachable covering.

Referring now to FIG. 2, means that are well-known in the art for the avoidance of inadvertent needle-stick can optionally be included within sealing member 108 to retract stylet 106 under spring action into sealing member 108 when spring release button 130 is pressed. In the embodiment of FIG. 2, stylet retaining block 202 compresses spring 204 and is retained by trigger 206 which engages a depression in stylet retaining block 202. Spring release button 130 releases spring 204, whereby stylet 106 is rapidly withdrawn into sealing member 108.

Referring again to FIG. 2, the device of the present invention further optionally comprises a detachable cover 208 engaging sealing member 108 and substantially enclosing catheter 104, stylet 106 and fitting 102. The material of the cover is not particularly limited, and can be of a rigid polymer or metal. In embodiments comprising a longer stylet, or a highly arcuate form, the cover can also be non-linear to facilitate its removal in use.

Figure 3:
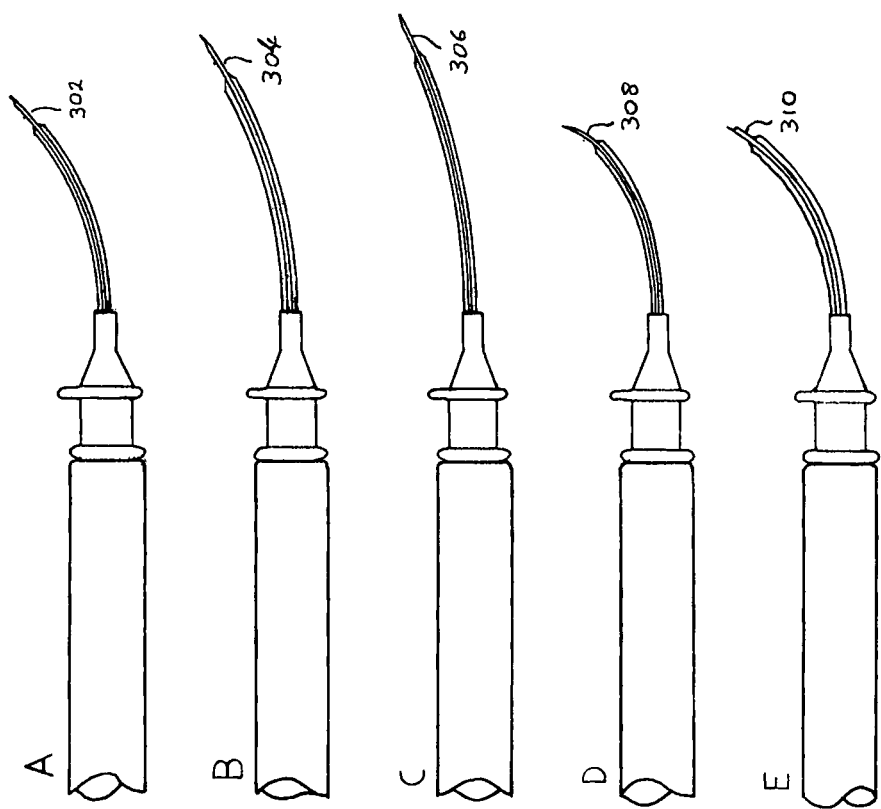
FIG. 3 shows embodiments of the catheterization device of the present invention comprising various preformed arcuate stylets: A-C circular arcs of differing radii; D an elliptical arc; E an irregular arc.

Referring now to FIG. 3, there catheterization devices according to the present invention comprising various different preformed arcuate stylets: circular arcs of different stylet radii 302, 304, 306; an elliptical stylet 308; and an irregular stylet 310 that is not elliptical or circular.

Figure 4:
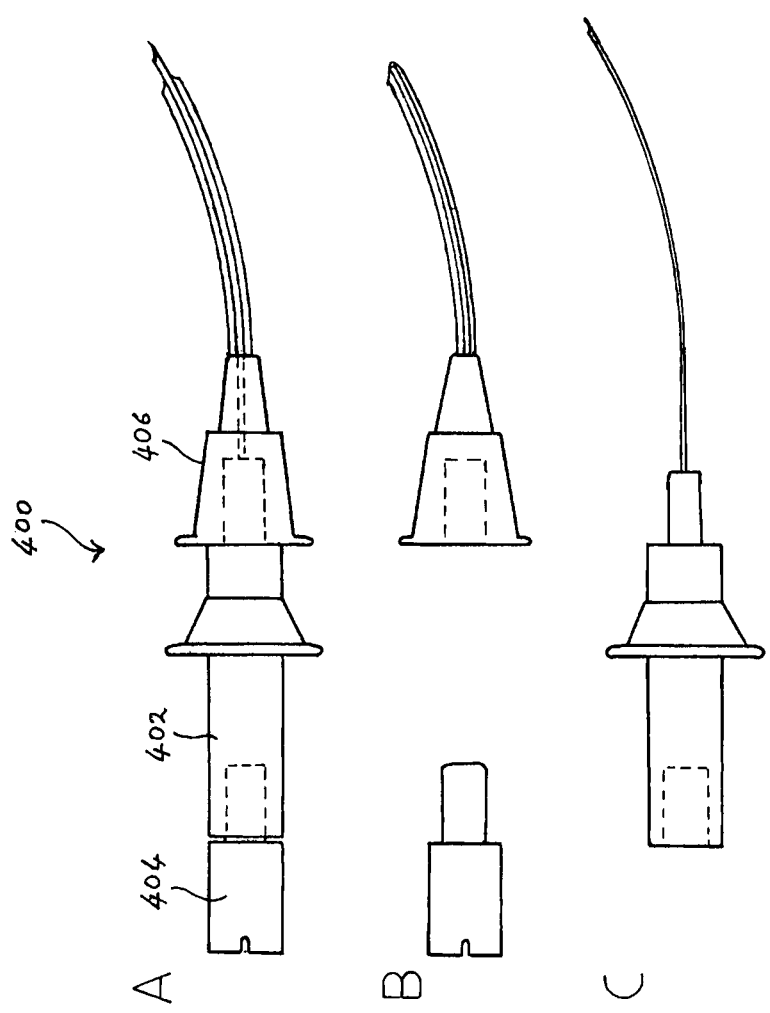
FIG. 4 shows an alternative embodiment of the catheterization device according to the present invention comprising a two-piece sealing member. A assembled; B and C disassembled.

Referring now to FIG. 4, an alternative embodiment 400 is shown in which the sealing member comprises two parts 402, 404. Fitting 406 is mounted to a first portion 402 of the sealing member, and a second portion 404 of the sealing member sealingly engages the first portion 402 to perfect the seal. The stylet is affixed to the first portion 402.

A method of use of the device of the present invention will now be described for illustrative purposes. The optional cover 208, if present, is removed and the stylet tip 126 is placed upon the skin of a subject close to a target blood vessel. The tip of the stylet is inserted into the vein by causing the tip to substantially traverse the arcuation of the stylet. Thus, for an embodiment in which the stylet is in the form of an arc of a circle, the tip is caused to traverse a substantially similar arc in passing from the skin to the blood vessel of a subject. By this means, the tip of the stylet can penetrate the skin at a large acute angle with respect to the skin surface, while the tip can subsequently enter the blood vessel at a smaller acute angle that is more nearly parallel with respect to the surface of the skin. Once the stylet has penetrated the blood vessel, the stylet is withdrawn while the catheter remains in place. In the embodiments of FIGS. 1 and 2, the stylet is retracted by pressing spring release button 130. In the embodiments of FIG. 4, the first portion 402 of the sealing member and stylet 106 are withdrawn as a unit, and, optionally, the second portion of the sealing member 404 can be detached from the first portion 402 and mounted to the fitting for a temporary seal.

A method for the use of a device of the present invention in which the stylet 114 is a tubular body such as a syringe needle will now be described for illustrative purposes. The optional cover, if present, is removed and the stylet tip 116 is placed upon the skin of a subject close to a target blood vessel. Next, the tip of the stylet is inserted into the blood vessel by causing the tip to substantially traverse the arcuation of the stylet. Upon penetration of the target blood vessel by the tubular stylet, blood flows through the tubular stylet and enters the tubular fitting 102. The appearance of blood in the tubular fitting 102 provides a visual cue to a user to cease further insertion of the stylet tip 126, thereby minimizing the risk that the stylet penetrates through the blood vessel into the surrounding tissue. The stylet 106 is withdrawn while the distal end 124 of the catheter 104 remains in place within the blood vessel and the stylet is retracted.

The device of the present invention provides a number of advantages over the prior art. The preformed arcuate stylet permits catheterization of blood vessels for which a direct approach is blocked by bone or other obstruction. The arcuate stylet can penetrate the vein wall at a more acute angle with respect to the vein wall, whereby the risk of passing through the opposite vein wall is lessened. Thus, vein wall damage is decreased and bleeding into the tissues is lessened. These advantages are of particular benefit in the treatment of elderly patients or in the catheterization of veins of intravenous drug users, whose veins may already be damaged. The preformed arcuate stylet eliminates the risk of catheter damage that could accrue if bending of the stylet were attempted after the catheter was assembled to the stylet.

While the present invention has been discussed within the context of intravenous catheterization, it will be readily appreciated that the invention can be used in other medical and veterinary contexts and for other purposes. In particular, the invention should not be construed as being limited to only intravenous applications.

Although the present invention has been described in considerable detail with reference to certain preferred versions thereof, other versions are possible and can be envisaged within the scope and spirit of the present invention. Therefore, the spirit and scope of the appended claims should not be limited to the description of the preferred versions contained herein.

Now that the invention has been described:
What is claimed is:

1. A catheterization device comprising:
   a fitting comprising a proximal end, a tapered distal end, and an interior surface;
   a flexible catheter comprising a tapered distal end, a proximal end, and an interior surface, the proximal end of said flexible catheter mounted to the distal end of said fitting, the interior surfaces of the flexible catheter and the fitting in fluid communication;
   a preformed rigid stylet having an arc shape, the preformed rigid stylet including a hollow body with a first end, a second end with a tip having a hollow-ground point, the tip is adapted for penetrating tissue and drawing blood from a blood vessel, the preformed rigid stylet disposed within said flexible catheter from the proximal end of said flexible catheter to the distal end of said flexible catheter, the tip of the preformed rigid stylet extending from the distal end of said flexible catheter;
   a tubular sealing member detachably mounted to the proximal end of said fitting, the tubular sealing member seals the proximal end of the fitting; and
   a retaining block located inside the tubular sealing member;
   the distal end of the preformed rigid stylet is attached to the retaining block, the retaining block retracts the preformed rigid stylet into the tubular sealing member;
   the blood enters the catheterization device through the hollow-ground point on the tip and flows from the rigid stylet to the fitting.

2. The catheterization device according to claim 1, wherein said fitting comprises a female luer fitting.

3. The catheterization device according to claim 1, further comprising a detachable covering mounting to said tubular sealing member and substantially enclosing the flexible catheter, the preformed rigid stylet, and the fitting.

4. The catheterization device according to claim 1, wherein the arc shape of said preformed rigid stylet is a circle.

5. The catheterization device according to claim 4, wherein the circle has a radius from about 1.5 inches to about 12 inches.

6. The catheterization device according to claim 1, wherein the preformed rigid stylet has a length from about 0.5 inches to about 4 inches.

7. The catheterization device according to claim 1, wherein the arc shape of said preformed rigid stylet is an ellipse.

8. The catheterization device according to claim 1, wherein the arc shape of said preformed rigid stylet is an irregular arc.

9. The catheterization device according to claim 1, wherein the tubular sealing member comprises a plurality of detachable parts.

10. A method for intravenous catheterization using the catheterization device according to claim 1, the method comprising:
    (a) placing the tip of the preformed rigid stylet of the catheterization device according to claim 1 upon the skin of a subject proximal to a vein;
    (b) inserting the hollow-ground point of the tip of the preformed rigid stylet into said vein by causing the tip to substantially traverse the arc shape of said preformed rigid stylet;
    (c) withdrawing blood from the vein;
    (d) withdrawing the preformed rigid stylet from the catheter after the blood appears in the fitting; and
    (e) detaching the sealing member from the fitting.

11. The catheterization device according to claim 1, further including at least one projection protruding from an outer surface of the fitting.

12. A catheterization device comprising:
    a fitting comprising a proximal end adapted for mounting to a fluid delivery or collection device, a tapered distal end, an outer surface, and an interior surface;
    a flexible catheter comprising a tapered distal end, a proximal end, and an interior surface, the proximal end of said flexible catheter mounted to the distal end of said fitting, the interior surfaces of the flexible catheter and the fitting in fluid communication;
    a tubular sealing member detachably mounted to the proximal end of said fitting, the tubular sealing member including a first part, a second part, an outer surface, an interior surface, the first part having a first end connected to the fitting and a second end connected to the second part; and a preformed rigid stylet having an arc shape, the preformed rigid stylet including a hollow body with a first end, a second end with a tip having a hollow-ground point, the tip is adapted for penetrating tissue and to draw blood from a blood vessel, the preformed rigid stylet disposed within said flexible catheter from the proximal end of said flexible catheter to the distal end of said flexible catheter, the tip of the preformed rigid stylet extending from the distal end of said flexible catheter;

a releasing mechanism including a retaining block, a compressed spring located in the interior surface of the tubular sealing member between a distal end of the sealing member and the retaining block, a trigger engaging a depression on the retaining block, and a release button located on the outer surface of the tubular sealing member and operatively connected to the retaining block and the compressed spring;

the first end of the preformed rigid stylet is attached to the retaining block inside the tubular sealing member, when the release button is pressed, the retaining block with the first end of the stylet retracts into the tubular sealing member;

the blood enters the catheterization device through the hollow-ground point on the tip and flows from the rigid stylet to the fitting.

* * * * *